US010081794B2

(12) United States Patent
Arinzeh et al.

(10) Patent No.: US 10,081,794 B2
(45) Date of Patent: Sep. 25, 2018

(54) SYSTEM AND METHOD FOR ELECTROSPUN BIODEGRADABLE SCAFFOLD FOR BONE REPAIR

(75) Inventors: Treena Lynne Arinzeh, West Orange, NJ (US); Tamunotonye Briggs, Edison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 884 days.

(21) Appl. No.: 14/111,638

(22) PCT Filed: Apr. 13, 2012

(86) PCT No.: PCT/US2012/033688
§ 371 (c)(1),
(2), (4) Date: Dec. 10, 2014

(87) PCT Pub. No.: WO2012/142533
PCT Pub. Date: Oct. 18, 2012

(65) Prior Publication Data
US 2015/0087062 A1 Mar. 26, 2015

Related U.S. Application Data
(60) Provisional application No. 61/475,191, filed on Apr. 13, 2011.

(51) Int. Cl.
| | |
|---|---|
| *C12N 5/077* | (2010.01) |
| *A61L 27/26* | (2006.01) |
| *A61L 27/38* | (2006.01) |
| *A61L 27/46* | (2006.01) |
| *A61L 27/54* | (2006.01) |
| *A61L 27/56* | (2006.01) |

(52) U.S. Cl.
CPC ............ *C12N 5/0654* (2013.01); *A61L 27/26* (2013.01); *A61L 27/3834* (2013.01); *A61L 27/46* (2013.01); *A61L 27/54* (2013.01); *A61L 27/56* (2013.01); *A61L 2300/252* (2013.01); *A61L 2300/414* (2013.01); *A61L 2300/602* (2013.01); *A61L 2300/802* (2013.01); *A61L 2430/02* (2013.01); *C12N 2533/30* (2013.01); *C12N 2537/00* (2013.01)

(58) Field of Classification Search
None
See application file for complete search history.

(56) References Cited

U.S. PATENT DOCUMENTS

| | | | |
|---|---|---|---|
| 4,846,835 | A | 7/1989 | Grande |
| 5,030,225 | A | 7/1991 | Aebischer et al. |
| 5,250,843 | A | 10/1993 | Eichelberger |
| 5,353,498 | A | 10/1994 | Eillion |
| 5,486,359 | A | 1/1996 | Caplan |
| 5,522,879 | A | 6/1996 | Scopelianos |
| 5,626,861 | A | 5/1997 | Laurencin et al. |
| 5,666,467 | A | 9/1997 | Colak |
| 5,681,873 | A | 10/1997 | Norton et al. |
| 5,766,618 | A | 6/1998 | Laurencin et al. |
| 5,811,094 | A | 9/1998 | Caplan |
| 5,827,735 | A | 10/1998 | Young |
| 5,842,193 | A | 11/1998 | Eichelberger |
| 5,906,934 | A | 5/1999 | Grande et al. |
| 5,955,529 | A | 9/1999 | Imai et al. |
| 6,095,148 | A | 8/2000 | Shastri et al. |
| 6,165,486 | A | 12/2000 | Marra et al. |
| 6,174,333 | B1 | 1/2001 | Kadiyala |
| 6,214,369 | B1 | 4/2001 | Grande et al. |
| 6,306,424 | B1 | 10/2001 | Vyakarnam |
| 6,355,239 | B1 | 3/2002 | Bruder |
| 6,387,367 | B1 | 5/2002 | David-Sproul |
| 6,464,983 | B1 | 10/2002 | Grotendorst |
| 6,472,210 | B1 | 10/2002 | Holy et al. |
| 6,482,231 | B1 | 11/2002 | Abatangelo |
| 6,489,165 | B2 | 12/2002 | Bhatnager et al. |
| 6,511,511 | B1 | 1/2003 | Slivka et al. |
| 6,541,024 | B1 | 4/2003 | Kadiyala |
| 6,652,872 | B2 | 11/2003 | Nevo et al. |
| 6,685,956 | B2 | 2/2004 | Chu |
| 6,689,166 | B2 | 2/2004 | Laurencin et al. |
| 6,689,374 | B2 | 2/2004 | Chu |
| 6,730,252 | B1 | 5/2004 | Teoh et al. |
| 6,783,712 | B2 | 8/2004 | Slivka et al. |

(Continued)

FOREIGN PATENT DOCUMENTS

| | | |
|---|---|---|
| CN | 101856510 B | 5/2010 |
| WO | WO 2005/118216 A1 | 12/2005 |

(Continued)

OTHER PUBLICATIONS

Kim, Taek Gyoung, Doo Sung Lee, and Tae Gwan Park. "Controlled protein release from electrospun biodegradable fiber mesh composed of poly (ε-caprolactone) and poly (ethylene oxide)." International journal of pharmaceutics 338.1 (2007): 276-283.*

Zeng, Jing, et al. "Ultrafine fibers electrospun from biodegradable polymers." Journal of Applied Polymer Science 89.4 (2003): 1085-1092.*

Zeng, Jing, et al. "Enzymatic degradation of poly (L-lactide) and poly (ε-caprolactone) electrospun fibers." Macromolecular bioscience 4.12 (2004): 1118-1125.*

Cho, Wan Jin, et al. "Characterization of Hydrophilized PCL Electrospun Sheet as an Efective Guided Bone Regeneration Membrane." Key Engineering Materials. vol. 342. Trans Tech Publications, 2007. (Year: 2007).*

Li, Xiaogiang, et al. "Encapsulation of proteins in poly (L-lactide-co-caprolactone) fibers by emulsion electrospinning." Colloids and Surfaces B: Biointerfaces 75.2 (2010): 418-424. (Year: 2010).*

(Continued)

*Primary Examiner* — Robert J Yamasaki
(74) *Attorney, Agent, or Firm* — McCarter & English, LLP

(57) ABSTRACT

This invention relates a structure and system for growth factor incorporation which can improve the osteogenic differentiation of hMSCs, for potential bone regeneration and bone growth applications or used alone for bone repair or growth applications. The system comprises a biodegradable polyester, a hydrophilic polymer, a growth factor and optionally a bioceramic.

7 Claims, 9 Drawing Sheets

(56) References Cited

U.S. PATENT DOCUMENTS

| | | |
|---|---|---|
| 6,790,455 B2 | 9/2004 | Chu |
| 6,790,528 B2 | 9/2004 | Wendorff et al. |
| 6,863,900 B2 | 3/2005 | Kadiyala |
| 7,012,106 B2 | 3/2006 | Yuan et al. |
| 7,022,522 B2 | 4/2006 | Guan et al. |
| 7,247,313 B2 | 7/2007 | Roorda et al. |
| 7,271,234 B2 | 9/2007 | Kohn et al. |
| 7,601,525 B2 | 10/2009 | Batich et al. |
| 7,619,901 B2 | 11/2009 | Eichelberger et al. |
| 7,767,221 B2 | 8/2010 | Lu et al. |
| 7,799,839 B2 | 9/2010 | Yun et al. |
| 7,803,574 B2 | 9/2010 | Desai |
| 7,824,701 B2 | 11/2010 | Binette et al. |
| 8,273,373 B2 | 9/2012 | Alsberg et al. |
| 2002/0004039 A1 | 1/2002 | Reid et al. |
| 2002/0034796 A1 | 3/2002 | Shastri et al. |
| 2002/0173213 A1 | 11/2002 | Chu et al. |
| 2003/0054035 A1 | 3/2003 | Chu et al. |
| 2003/0069369 A1 | 4/2003 | Belenkaya et al. |
| 2003/0077311 A1 | 4/2003 | Vyakarnam et al. |
| 2003/0211130 A1 | 11/2003 | Sanders et al. |
| 2004/0018226 A1 | 1/2004 | Wnek et al. |
| 2005/0095695 A1 | 5/2005 | Shindler et al. |
| 2005/0196423 A1 | 9/2005 | Batich et al. |
| 2006/0057377 A1 | 3/2006 | Harrison et al. |
| 2006/0094320 A1 | 5/2006 | Chen et al. |
| 2006/0128012 A1 | 6/2006 | Arinzeh et al. |
| 2006/0198865 A1 | 9/2006 | Freyman et al. |
| 2006/0204539 A1 | 9/2006 | Atala et al. |
| 2006/0240064 A9 | 10/2006 | Hunter et al. |
| 2007/0179594 A1 | 8/2007 | Llanos et al. |
| 2007/0267725 A1 | 11/2007 | Lee et al. |
| 2008/0009599 A1 | 1/2008 | East et al. |
| 2008/0112150 A1 | 5/2008 | Jones |
| 2008/0206343 A1 | 8/2008 | Edinger et al. |
| 2008/0220054 A1* | 9/2008 | Shastri et al. ......... A61K 47/34 424/443 |
| 2008/0246126 A1 | 10/2008 | Bowles et al. |
| 2009/0028921 A1* | 1/2009 | Arinzeh ................ A61F 2/28 424/423 |
| 2009/0048358 A1 | 2/2009 | Kim |
| 2009/0325296 A1 | 12/2009 | Arinzeh et al. |
| 2010/0078771 A1 | 4/2010 | Barth et al. |
| 2010/0078776 A1 | 4/2010 | Barth et al. |
| 2010/0173158 A1 | 7/2010 | Furuzono et al. |
| 2010/0233807 A1 | 9/2010 | Arinzeh et al. |
| 2010/0303881 A1 | 12/2010 | Hoke et al. |
| 2010/0324697 A1 | 12/2010 | Arinzeh et al. |
| 2015/0087062 A1 | 3/2015 | Arinzeh et al. |

FOREIGN PATENT DOCUMENTS

| | | |
|---|---|---|
| WO | WO 2006/068809 | 6/2006 |
| WO | WO 2006/095021 A1 | 9/2006 |
| WO | WO 2008/055038 A2 | 5/2008 |
| WO | WO 2008093341 A2 * | 8/2008 ............. A61L 27/46 |

OTHER PUBLICATIONS

Van Royen, P., et al. "Characterisation of the surface composition in electrospun nanowebs with static secondary ion mass spectrometry (S-SIMS)." Talanta 71.4 (2007): 1464-1469. (Year: 2007).*
Lin, Kenneth, et al. "Reducing electrospun nanofiber diameter and variability using cationic amphiphiles." Polymer 48.21 (2007): 6384-6394. (Year: 2007).*
PCT International Search Report and Written Opinion for PCT/US2012/033688 dated Sep. 24, 2012.
PCT/US2012/033688, filed Apr. 13, 2012, WO 2012/142533.
U.S. Appl. No. 61/475,191, filed Apr. 13, 2011.
Arinzeh, T. et al, Allogeneic mesenchymal stem cells regenerate bone in a critical-sized canine segmental defect, Journal of Bone and Joint Surgery American, 2003, 85-A(1):1927-35.
Arinzeh, T. et al.,In vivo Evaluation of a Bioactive Scaffold for Bone Tissue Engineering, J. Biomed. Mat. Res., 2002, 62:1-13.
Bhattarai, et al., Novel Biodegradable Electrospun Membrane: Scaffold for Tissue Engineering, Biomaterials, vol. 25, No. 13, pp. 2595-2602, 2004.
Bruder, S. P. et al., Bone Regeneration by Implantation of Purified, Culture-Expanded Human Mesenchymal Stem Cells, J. Orthop. Res., 1998, 16:155-162.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Collins, M. N. et al., Comparison of the effectiveness of four different crosslinking agents with hyaluronic acid hydrogel films for tissue-culture applications, Journal of Applied Polymer Science, 104(5):3183-91, 2007.
Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.
Fujihara, et al., Guided Bone Regeneration Membrane Made of Polycaprolactone/Calcium Carbonate Composite Nano-fibers, Biomaterials, 26, pp. 4139-4147, 2005.
Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.
Jin et al., "Human Bone Marrow Stromal Cell Responses on Electrospun Silk Fibroin Mats", Biomaterials, 2004, vol. 25, pp. 1039-1047.
Kadiyala, S. et al., Culture-expanded, bone marrow-derived mesenchymal stem cells can regenerate a critical-sized segmental bone defect, Tissue Engineering, 1997, 3(2):173-185.
Kang, S. W. et al., Ply(lactic-co-glycolic acid) microspheres as an injectible scaffold for cartilage tissue engineering, Tissue Engineering, 2005, 11(3-4):438-47.
Kuo, C. K. et al., Cartilage tissue engineering: its potential and uses, Current Opinion in Rheumatology, 2006, 18(1):64-73.
Laurencin, C.T. "Tissue Engineering: Orthopedic Applications," Ann. Rev. Biomed. Eng'g 1:19-46 (1999).
Li et al., Electrospun Silk-BMP-2 Scaffolds for Bone Tissue Engineering, Biomaterials, 27, pp. 3115-3124, 2006.
Li, et al., Biological Response of Chondrocytes Cultured in Three-Dimensional Nanofibrous Poly(€-caprolactone) Scaffolds, J. Biomed. Mat. Res. Part A., 67A, 4, pp. 1105-1114, 2003.
Li, et al., Electrospun Nanofibrous Structure: A Novel Scaffold for Tissue Engineering, Journal of Biomedical Mat. Res., vol. 60, Issue 4, pp. 613-621, 2002.
Li, Wan-Ju et al., Multilineage Differentiation of Human Mesenchymal Stem Cells in a Three-Dimensional Nanofibrous Scaffold, Biomaterials, vol. 26, No. 25, pp. 5158-5166, 2005.
Luu et al., "Development of a Nanostructured DNA Delivery Scaffold via Electrospinning of PLGA and PLA-PEG block copolymers". Journal of Controlled Release, 2003, vol. 89, pp. 341-353.
Nettles et al., Potential Use of Chitosan as a Cell Scaffold Material for Carilage Tissue Engineering, Tissue Engineering, vol. 8, No. 6, pp. 1009-1016, 2002.
Rezwan et al., Biodegradable and Bioactive Porous Polymer/inorganic Composite Scaffolds for Bone Tissue Engineering, Biomaterials, 27, pp. 3413-3431, 2006.
Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shanmugasundaram, et al., Microscale Versus Nanoscale Scaffold Architecture for Mesenchymal Stem Cell Chondrogenesis, Tissue Engineering: Part A, vol. 60, No. 00, pp. 1-10, 2010.
Shanmugasundaram, S. et al., Regulation of human mesenchymal stem cell chondrogenesis by scaffold geometry and mechanical properties, Society for Biomaterials Annual Meeting, 2009.

(56) References Cited

OTHER PUBLICATIONS

Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Shin et al., In Vivo Bone Tissue Engineering Using Mesenchymal Stem Cells on a Novel Electrospun Nanofibrous Scaffold, Tissue Engineering, 10, pp. 33-41, 2004.
Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.
Wan-Ju, et al., Biological Response of Chondrocytes Cultrued in Three-Dimensional Nanofibrous Poly(€-caprolactone) Scaffolds, J. Biomed. Mater. Res. 67A:1105-1114, 2003.
Wei et al., Structural and Properties of Nano-Hydroxyapatite/Polymer Composite Scaffolds for Bone Tissue Engineering, Biomaterials, 25, pp. 4749-4757, 2004.
Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.
Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.
Yoshimoto et al., A Biodegradable Nanofiber Scaffold by Electrospinning and its Potential for Bone Tissue Engineering, Biomaterials, 24, pp. 2077-2082, 2003.
Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.
Zhao, et al., Preparation and Properties of Electrospun Poly(Vinylidene Fluoride) Membranes, Journal of Applied Polymer Science, vol. 97, 466-474, 2005.
Zhou et al., In Vitro Bone Engineering Based on Polycaprolactone and Polycaprolactone-Tricalcium Phosphate Composites, Polym. Int. 56, pp. 333-342, 2007.
Zong et al., Electrospun Non-woven Membranes as Scaffolds for Heart Tissue Constructs. 226th ACS National Meeting, 2003. 2003.
Patlolla, A., Collins, G., Livingston Arinzeh, T. 2010. Solvent Dependent Dimensional and Structural Changes in Electrospun Ceramic Fiburous Composites for Bone Tissue Engineering. Acta Biomaterialia. 6(1): 90-101.
Zhu, X., et al., Protein Adsorption and zeta potentials of a biphasic calcium phosphate ceramic under various conditions. Journal of Biomedical Materials Research Part B: Applied Biomaterials, 2007. 82B(1): p. 65-73.
U.S. Appl. No. 11/291,701, filed Dec. 1, 2005, US-2006-0128012-A1.
U.S. Appl. No. 12/141,340, filed Jun. 18, 2008, US-2009-0028921-A1.
U.S. Appl. No. 12/411,320, filed Mar. 25, 2009, US-2009-0325296-A1.
U.S. Appl. No. 12/661,242, filed Mar. 12, 2010, US-2010-0233234-A1.
U.S. Appl. No. 12/661,264, filed Mar. 12, 2010, US-2010-0324697-A1.
U.S. Appl. No. 12/763,755, filed Apr. 20, 2010, US-2010-0233807-A1.
U.S. Appl. No. 13/097,657, filed Apr. 29, 2011, US-2010-0274742-A1.
U.S. Appl. No. 13/210,806, filed Aug. 16, 2011, US-2011-0300626-A1.
U.S. Appl. No. 13/651,296, filed Oct. 12, 2012, US-2013-0052254-A1.
U.S. Appl. No. 14/381,496, filed Aug. 27, 2014, US-2016-0000974-A1.
PCT/US2005/043876, filed Dec. 1, 2005, WO 2006/068809.
PCT/US2008/067322, filed Jun. 18, 2008, WO 2005/157594.
PCT/US2012/050156, filed Aug. 9, 2012, WO 2013/023064.

\* cited by examiner

SYSTEM AND METHOD FOR ELECTROSPUN BIODEGRADABLE SCAFFOLD FOR BONE REPAIR

FIELD OF THE INVENTION

This invention relates to electrospun composite scaffolds useful for cell proliferation, bone repair and bone growth, to a process for making and a method of using the scaffolds of the invention.

BACKGROUND OF THE INVENTION

Musculoskeletal diseases affect nearly 25% of the American population and is expected to increase with the growing aging population. Furthermore, bone fractures represent a majority of all traumas that take place on the battlefield. Traditional treatment options for these diseases employ autografts and allografts, tissue harvested from one's own bone or donated human cadaver bone, respectively. However issues with tissue scarcity, donor site morbidity, subsequent invasive surgeries in the case of autografts; and possible donor transmitted diseases in the case of allografts makes these treatment options less than ideal. Moreover, processed acellular allografts have limited success in the healing because, although they provide a mechanically compatible scaffold to fill a bone void, these grafts lack viable biological components such as growth factors and cells to initiate osteoinduction, which is the process of initiating the induction of undifferentiated cells towards the osteogenic lineage.

Recent advances in fields of material science, scaffold fabrication and recombinant DNA technology have provided engineers with tools to develop tissue engineered scaffolds to regenerate bone tissue. The desired outcome of tissue engineered bone grafts is the replacement of the graft with new bone growth, therefore an ideal tissue engineered bone graft should be osteoinductive, bioresorbable, and mechanically compatible to host bone.

Bone is a composite tissue comprised of organic and inorganic phases, various cell types, and growth factors. On the nanoscopic level, the extracellular matrix (ECM) of bone consists mainly of an organic phase in the form of fibrillar Type I collagen and an inorganic phase in the form of hydroxyapatite [HA, $Ca_{10}(PO_4)_6(OH)_2$] particles. The ECM provides mechanical and structural support for surrounding cell types such as osteoblasts, osteocytes and osteoclasts. The precursors of these cell types are osteoprogenitors which originate from mesenchymal stem cells (MSCs). The ECM also serves as a reservoir for growth factors.

Growth factors are signaling proteins that direct cellular proliferation, differentiation, angiogenesis, apoptosis, and even de-differentiation. Growth factors are bound in their latent form to the extracellular matrix (ECM) to sulfated glycosaminoglycans: heparin or heparan sulfate. Upon release from the ECM, growth factors work synergistically and antagonistically in a coordinated, temporal manner to direct the functions of bone regeneration.

Due to proteolytic degradation, growth factors have short half-lives, which is the time to deactivate half of its bioactivity. Therefore, the systemic delivery of growth factors during fracture healing would be ineffective. Local delivery of the growth factor at the site of target is a more effective means of growth factor administration. Recent advances in the development of drug delivery vehicles such as microspheres, hydrogels, and electrospun scaffolds have been promising in the local administration of growth factors.

Electrospinning has been recently utilized in the field of tissue engineering as a scaffold fabrication technique to prepare non-woven scaffolds with fiber diameters on the order of nanometers to microns. The high surface area-volume ratio of the fibers generated in the electrospinning process, makes it an ideal vehicle for various drug delivery applications. The main challenge in the administration of growth factors from electrospun scaffolds is preserving the bioactivity of the incorporated growth factor.

The growth factor can be incorporated at various times in relation to the electrospun composite of the invention, including pre-electrospun incorporation, absorption oro post electrospun incorporation. Pre-electrospun methods include those known in the art such as co-axial electrospinning, emulsion electrospinning and other alternative methods such as electrospinning growth factor encapsulated microspheres, and hydrophobic ion pairing. Post-electrospun growth factor incorporation methods include non-covalent adsorption and growth factor immobilization.

There are various tissue engineering applications for growth factor incorporated electrospun scaffolds such as wound healing, neural regeneration, and musculoskeletal and orthopedic applications.

There has been considerable research in developing growth factor incorporated electrospun scaffolds for the regeneration of tissue from the musculoskeletal system (bone, cartilage, skeletal muscle, etc.) with MSCs which under specific induction conditions can differentiate into osteoblasts, chondrocytes, adipocytes as well as other cell types.

BMP-2 incorporation in electrospun scaffolds is of interest in the osteogenic differentiation of MSCs. Human MSC gene expression of osteogenic markers Alkaline Phosphatase (AP) and Osteocalcin (OC) were upregulated on BMP-2 incorporated electrospun scaffolds compared to PLLA scaffolds without BMP-2.

As known in the art, BMP-2 is integral in mid-to-late stage osteogenic differentiation. Therefore, the release of bioactive BMP-2 is most effective when administered in a sustained manner. Electrospun scaffolds, as known in the art, have been prepared by co-axial electrospinning in which the core solution consisted of BMP-2 incorporated in PEO and the shell solution consisted of a blend of PCL and various concentrations of PEG to manipulate the release rate of BMP-2. Overall, AP activity was higher in hMSCs on scaffolds incorporated with BMP-2 compared to scaffolds without BMP-2. Furthermore, scaffolds prepared with the slow releasing BMP 2 formulation induced higher AP activity compared to scaffolds prepared with a fast releasing BMP-2 formulation. The in vivo analysis showed that de novo bone formation in cranial defects was enhanced with the BMP-2 incorporated scaffolds, with the slow releasing BMP-2 scaffold formulation inducing more bone formation compared to the fast releasing BMP-2 scaffold formulation.

Most growth factor incorporated electrospun scaffolds are comprised of polymers. The addition of a ceramic component to polymers would be an ideal model for bone regeneration because it would reflect the composition of bone in vivo. Investigation in the development of growth factor incorporated polymer/ceramic composite electrospun scaffolds is limited. BMP-2 incorporated PLGA/Hydroxyapatite (HA) composites prepared by emulsion electrospinning and non-covalent adsorption has been investigated.

Characterization of the release kinetics of BMP-2 from electrospun scaffolds revealed a high burst release of BMP-2 from the scaffold prepared by non-covalent adsorption. Furthermore, the effect of different concentrations of HA on the release of BMP-2 was investigated and it was found that increasing the concentration of HA in the composite from 5% (w/w) to 10% (w/w) led to a higher burst release which was thought to be attributed to the hydrophilicity of HA. Human MSCs attachment and viability was highest in preelectrospun BMP-2 incorporated scaffolds prepared with 10% (w/w) HA compared to pre-electrospun BMP-2 incorporated with 5% (w/w) HA, as well as post-electrospun BMP-2 incorporated scaffolds and scaffolds without BMP-2. Scaffolds prepared with BMP-2 improved the healing of critical sized defects in mice tibia.

The effect of BMP-2 incorporated in electrospun composites prepared with a combination of silk, PEO, HA, and BMP-2 by emulsion electrospinning, on the proliferation and osteogenic differentiation of hMSCs has also been investigated. Human MSCs seeded on the BMP-2 incorporated silk/PEO/HA composite had increased calcium deposition as well as higher BMP-2 gene expression compared to scaffolds prepared by the other formulations. This indicates that the PEO and HA enhanced the bioactivity of BMP-2 to initiate osteogenic differentiation of human MSCs.

Hematopoietic stem cells (HSCs) reside in adult bone marrow close to the endosteum. Under either stochastic or deterministic conditions, HSCs differentiate into the various blood cells such as neutrophils, monocytes/macrophages, basophils, eosinophils, erythrocytes, platelets, mast cells, dendritic cells, B and T lymphocytes. Platelets are anucleur cellular fragments, derived from the fragmentation of megakaryocytes. During fracture healing, thrombin activation initiates platelets to release Platelet Derived Growth Factor (PDGF) from the α-granules in its cytoplasm. PDGF is a 25 kDa dimeric glycoprotein that consists of two polypeptide chains linked by a disulfide bond. There are a total of four different polypeptide chains: A, B, C, D that form five different isomers of PDGF: PDGF-AA, PDGF-BB, PDGF-CC, PDGF-DD, and PDGFAB. MSCs and osteoblasts express PDGF receptor-β (PDGFR-β) during fracture healing which bind to the PDGF-BB isoform, which activates a signal transduction pathway that induces cell proliferation, chemotaxis and the upregulation of certain osteogenic markers.

BMPs are members of the transforming growth factor-β (TGF-β) family. The administration of BMP-2, a 26 kDa homodimeric glycoprotein, induces ectopic bone formation and has been implicated in embryonic limb bud formation and bone fracture healing. During fracture healing, BMPs are released from the ECM and bind to BMP receptors (BMPR-I and BMPR-II) on MSCs. This initiates a signal transduction cascade involving the phosphorylation of Smad proteins: Smad-1, Smad-5 and Smad-8, which form a complex with Smad-4 in the nucleus, activating gene expression for proliferation and osteogenic differentiation. BMP-2 is integral throughout the duration of osteogenic differentiation of hMSCs, and has been specifically expressed in the maturation phase of osteoblasts.

However, there remains a need for developing a reliable system for administering growth factors in a manner advantageous to affect bone repair. Further, new methods for growth factor bioactivity preservation must be further developed and investigated, especially with emphasis on the large scale up for possible medical device implementation.

SUMMARY OF THE INVENTION

There now has been developed a structure and system for growth factor incorporation which can improve the osteogenic differentiation of mesencymal stem cells (MSC) and related osteogenic progenitors, for potential bone regeneration and repair applications. More particularly, the invention relates to an electrospun composite scaffold comprising a polyester (poly alpha hydroxyl ester), a hydrophilic polymer and a growth factor or a protein. The scaffold of the invention can also be used alone for bone repair or growth applications Optionally, the electrospun composite scaffold of the invention may further comprise a bioceramic.

In one embodiment of the invention, the electrospun composite scaffold comprises polycaprolactone (PCL), polyethylene oxide (PEO), and Recombinant Human Platelet Derived Growth Factor-BB (PDGF-BB).

Another embodiment of the invention relates to a process to support cell proliferation and osteogenic activity comprising culturing human mesenchymal stem cells (hMSCs) on an electrospun composite scaffold comprising a polyester, a hydrophilic polymer and a growth factor or a protein.

Another embodiment of the invention relates to the use of the electrospun composite scaffold of the invention in bone repair applications and to support bone growth.

BRIEF DESCRIPTION OF THE DRAWINGS

So that those having ordinary skill in the art will have a better understanding of how to make and use the disclosed systems and methods, reference is made to the accompanying figures wherein.

DETAILED DESCRIPTION OF THE INVENTION

Figure 1A:
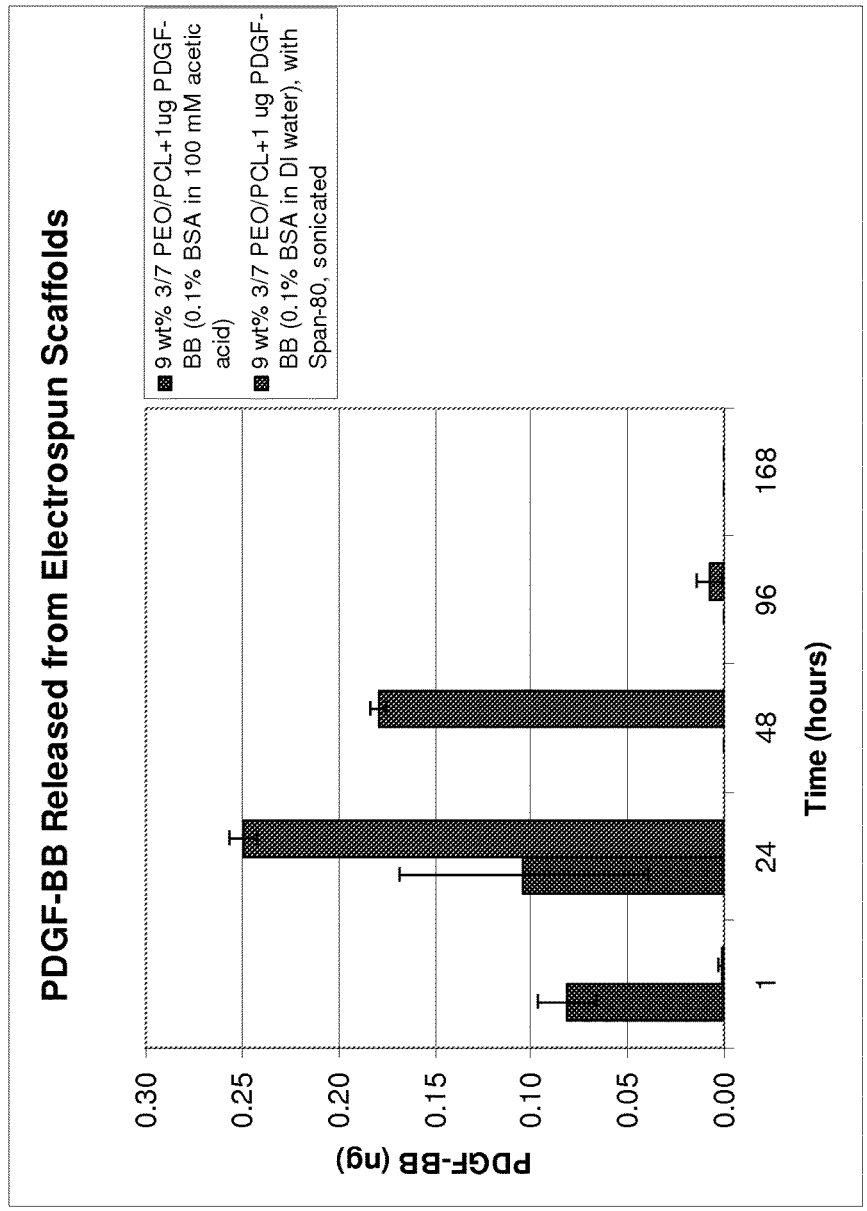
FIG. 1a shows release of PDGF-BB from electrospun scaffolds PDGF-BB released from 9 wt % 3/7 PEO/PCL with 1 μg PDGF-BB without Span®80 and without sonication: blue; and 9 wt % 3/7 PEO/PCL with 1 μg PDGF-BB with Span® 80 and sonicated: purple.
Figure 1:
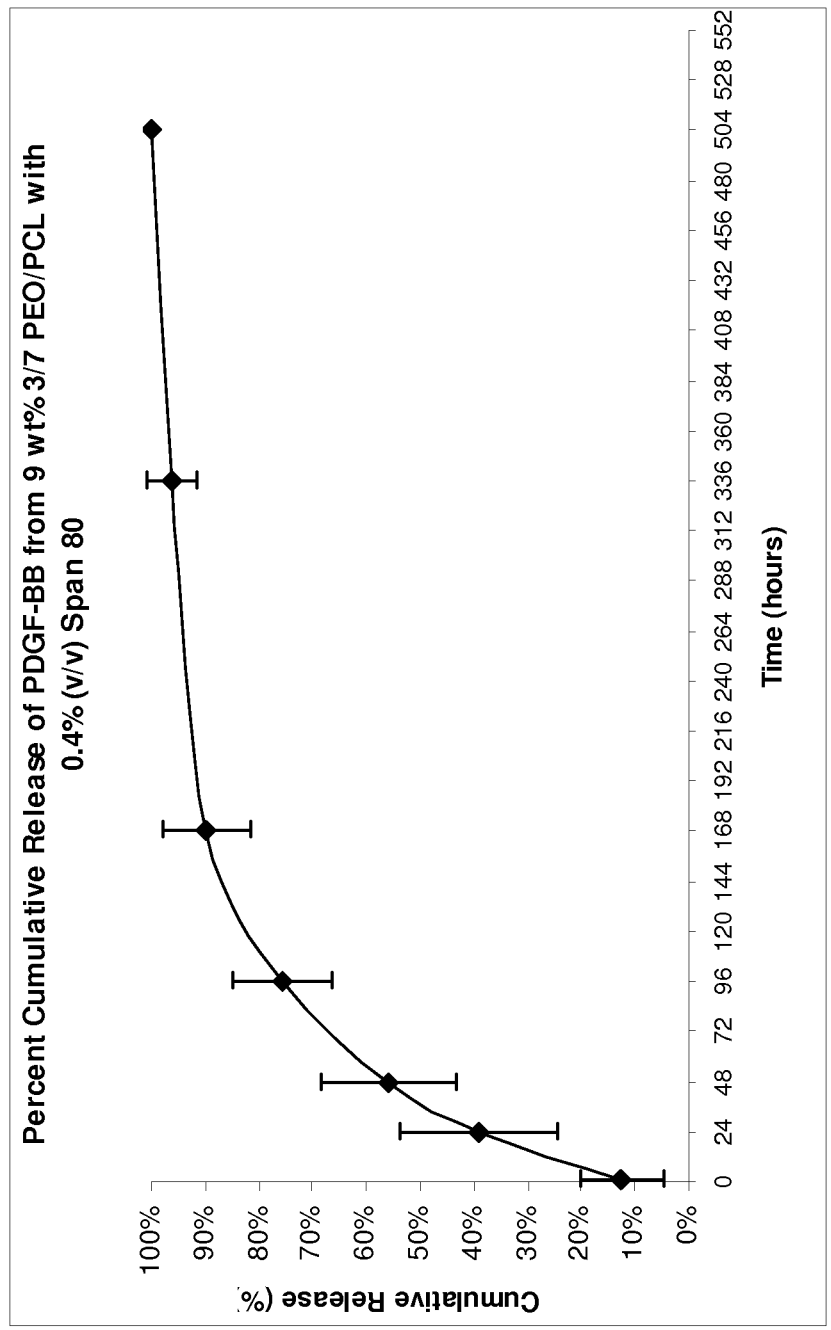
FIG. 1b shows Percent Cumulative Release of PDGF-BB from 9 wt % 3/7 PEO/PCL with Span® 80.

The electrospun composite scaffold of the invention most generally is comprised of polyester (poly alpha hydroxyl ester), a hydrophilic polymer and a growth factor or a protein.

The polyester of the invention includes, for example, polylactic acid, polyglycolic acid and polylactic co-glyocolic acid copolymers, which are chosen, in part by the speed of degradation desired for a particular purpose. In certain embodiments of the invention polycaprolactone (PCL) is a preferred component.

The hydrophilic polymers of the inventions are polymers such as, for example, polyethylene oxide, polyethylene glycol, polyvinyl alcohol, glycosaminoglycans, chitosan, sulfated dextran, sulfated cellulose and heparin sulfate. In certain embodiments of the invention polyethylene oxide (PEO) is a preferred component.

Growth factors useful in the invention include, for example, bone-morphogenetic protein (BMP), platelet derived growth factor-BB (PDGF-BB), vascular endothelia growth factor (VEGF) and transforming growth factor-beta (TGF-beta).

Optionally, the electrospun composite scaffold of the invention may further comprise a bioceramic, such as, for example, hydroxyapatite, tricalcium phosphate, biphasic calcium phosphates, calcium carbonate, calcium sulfate, and bioactive glass. Also included are biphasic bioceramics such as, for example, 20/80 Hydroxyapatite/β-Tricalcium phosphate (HA/β-TCP).

Electrospun composite consisting of PCL and HA alone or beta-TCP alone can be formed using the same conditions as described for the PCL containing 20/80 HA/TCP. Since HA is a stable ceramic and beta-TCP is a more soluble/relatively fast-degrading ceramic, the use of either of these ceramics in the composite may alter the overall degradation and bioactivity of the composite as compared to the PCL containing 20/80 HA/TCP. Since HA is more stable than beta-TCP, a composite consisting of HA alone may be advantageous for producing a more stable composite material wherein the ceramic component remains in the composite long-term. For a composite containing beta-TCP alone, this will result in a fast-degrading ceramic component which may have an effect on the overall bioactivity and may enhance the formation of an apatite on the composite because the surrounding solution becomes saturated with calcium and phosphate ions.

The scaffold may further comprise a non-ionic surfactant, such as, for example, Span® 80, or a cationic surfactant, such as, for example, cetyl trimethylammonium bromide (CTAB).

In a further embodiment of the invention the electrospun composite scaffold comprises a non-ionic surfactant such as, for example Span® 80.

In yet another embodiment of the invention, when the electrospun composite comprises a biphasic ceramic, it also may comprise a cationic surfactant such as, for example, cetyl trimethylammonium bromide (CTAB).

Another embodiment of the invention relates to a process to support cell proliferation and osteogenic activity comprising culturing human mesenchymal stem cells (hMSCs) on an electrospun composite scaffold comprising from about 70% to about 100% PCL and from about 0% to about 30% PEO, which may further comprise PDGF-BB.

Another embodiment of the invention relates to a process to support cell proliferation and osteogenic activity comprising culturing human mesenchymal stem cells (hMSCs) on an electrospun composite scaffold comprising about 9 wt % PCL+about 30% (w/w) 80/20 β-TCP/HA.

More particularly, the invention relates to an electrospun composite scaffold comprising polycaprolactone (PCL) and the biphasic ceramic: 80/20 β-Tricalcium phosphate/Hydroxyapatite (β-TCP/HA) can be used for the delivery of growth factors to enhance bone tissue growth. The composite scaffold consisting of PCL and the bioactive ceramic is described in U.S. patent application Ser. No. 12/141,340 for bone regeneration applications.

For growth factor delivery, PCL was combined with the hydrophilic polymer polyethylene oxide (PEO) at a ratio of between about 0%-30% PEO to about 70%-100% PCL to enhance the incorporation of hydrophilic growth factors/proteins. Said growth factor delivery can be done with or without the addition of the ceramic. However, when added the ceramic used is a biphasic ceramic: 80/20 β-TCP/HA was added to the polymer solutions of between about 9 wt %-17% wt PCL and about 9 wt %-about 17% wt 0-30/70-100 PEO/PCL at a concentration of 30% (w/w) with respect to polymer mass in chloroform. Recombinant human Platelet Derived Growth Factor-BB (PDGF-BB), a 25 kDa mitogenic growth factor, was incorporated into the solution of the polymers alone and in a dispersion of the polymers and ceramics. Initial in vitro release studies were conducted to predict the release kinetics and bioactivity of PDGF-BB using a model protein, lysozyme which has similar charge properties to PDGF-BB. Any growth factors in the class of transforming growth factors, including Bone Morphogenetic Protein could be utilized in lieu of PDGF-BB.

Some embodiments of the present invention utilize the polymers alone, without the ceramic component.

In studies of PDGF-BB release from electrospun scaffolds the quantity of PDGF-BB released from PCL over the 7 day study was nearly negligible compared to the PDGF-BB released from 30/70 PEO/PCL. It was further determined that for many applications requiring the release of PDGF-BB, the advantageous ration of PEO to PCL was about 30/70 PEO/PCL.

It was further determined that for some embodiments of the present invention the addition of the non-ionic surfactant, Span® 80, to the polymer solution followed by with or without ultrasonication prior to electrospinning sustained the release of PDGF-BB from the scaffold from 1 day without Span® 80 to at least 4 days with Span® 80 (FIGS. 1a. and b.).

For certain embodiments of the present invention, the initial in vitro release studies were conducted to predict the release kinetics and bioactivity of PDGF-BB using a model protein, lysozyme, which has similar charge properties to PDGF-BB.

It was observed that the biphasic ceramic β-TCP/HA had a significant effect on the release kinetics and bioactivity of the incorporated lysozyme from electrospun polymer/ceramic scaffolds compared to electrospun polymer scaffolds without β-TCP/HA. Furthermore, the addition of CTAB altered the release kinetics and retained the activity of lysozyme released from the scaffolds as well as conserved some of the secondary structure conformation of lysozyme adsorbed onto the surface.

Accordingly, in another embodiment of the present invention, PDGF-BB was incorporated in an electrospun polymer/ceramic composite comprising of polycaprolactone (PCL), and nanoparticles of biphasic ceramic, β-tricalcium phosphate (β-TCP) and hydroxyapatite (HA) and evaluated for release and bioactivity as determined by the growth and osteogenic differentiation of human MSCs. PDGF-BB was incorporated using phase separation by the addition of polyethylene oxide (PEO) and by examining a novel technique of incorporating a cationic surfactant.

PDGF-BB has an isoelectric point of 11.1 which would have an electrostatic attraction to the negative phosphate ions in the ceramic and may impede its release from the composite. Therefore, the cationic surfactant, hexadecyltrimethylammonium bromide (CTAB) was added to form a complex with the phosphate ions in certain embodiments of the present invention which would, in turn, reduce the electrostatic attraction between PDGF-BB and the biphasic ceramic, leading to the release of PDGF-BB from the electrospun scaffolds.

Figure 2:
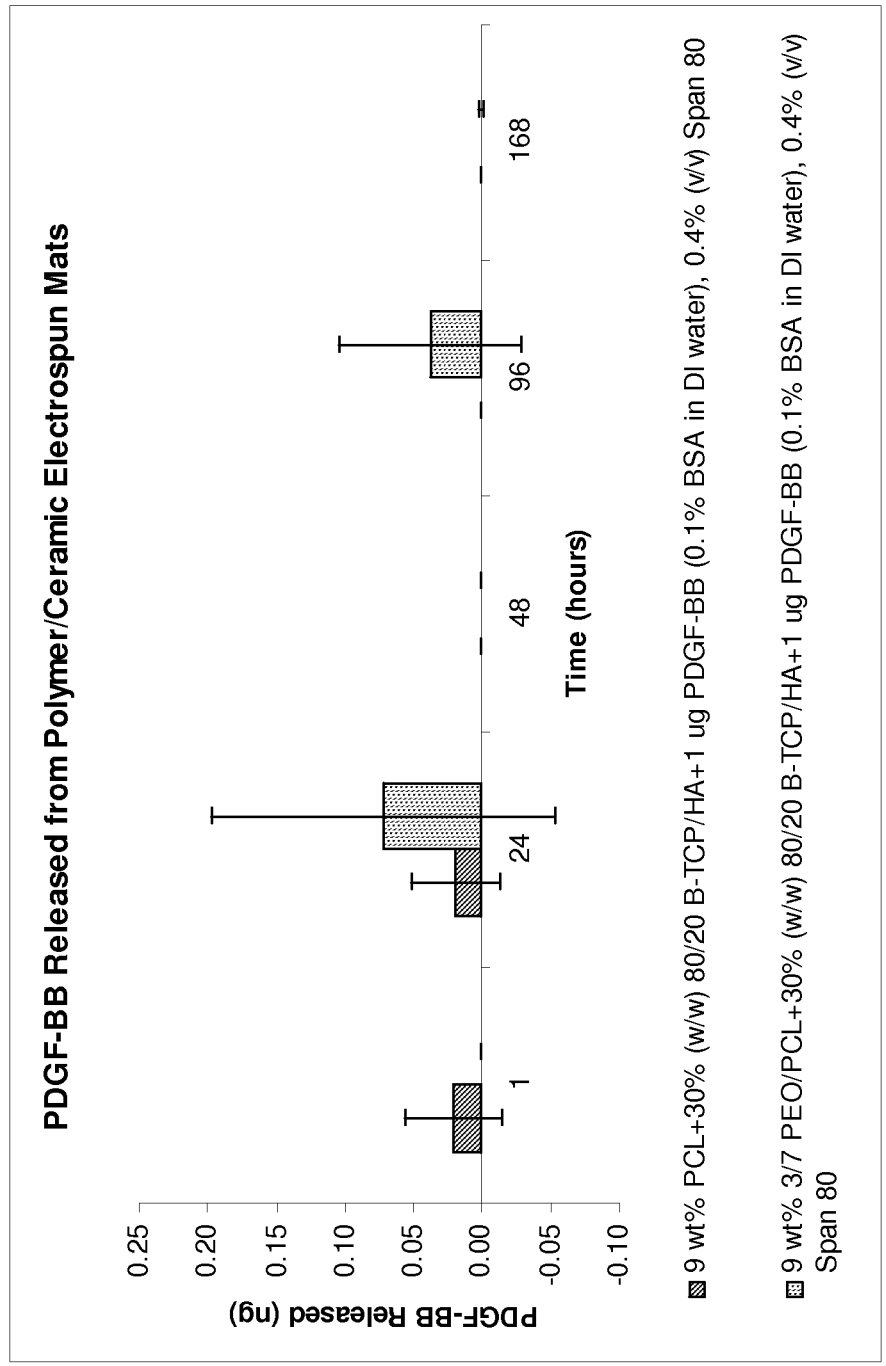
FIG. 2 shows PDGF-BB released from polymer/ceramic electrospun mats.
Figure 3:
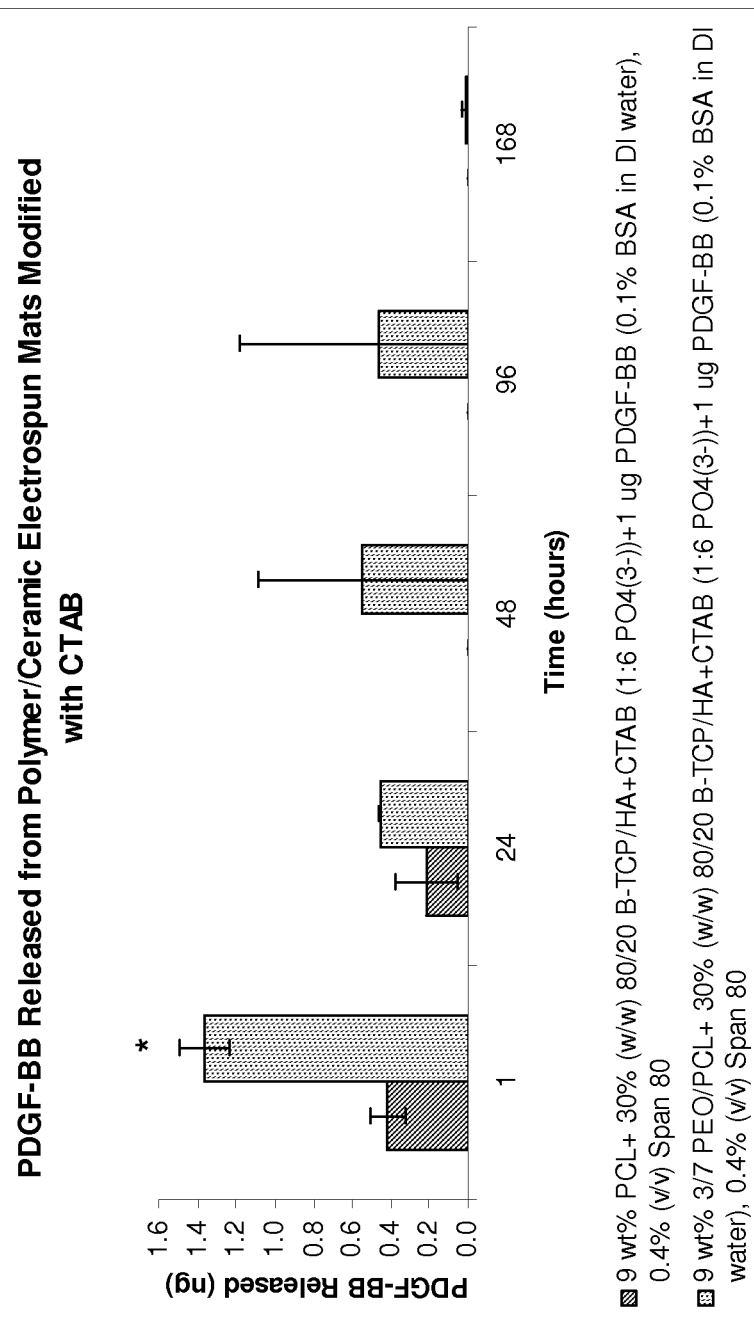
FIG. 3 shows PDGF-BB released from polymer/ceramic electrospun mats modified with CTAB.
Figure 4:
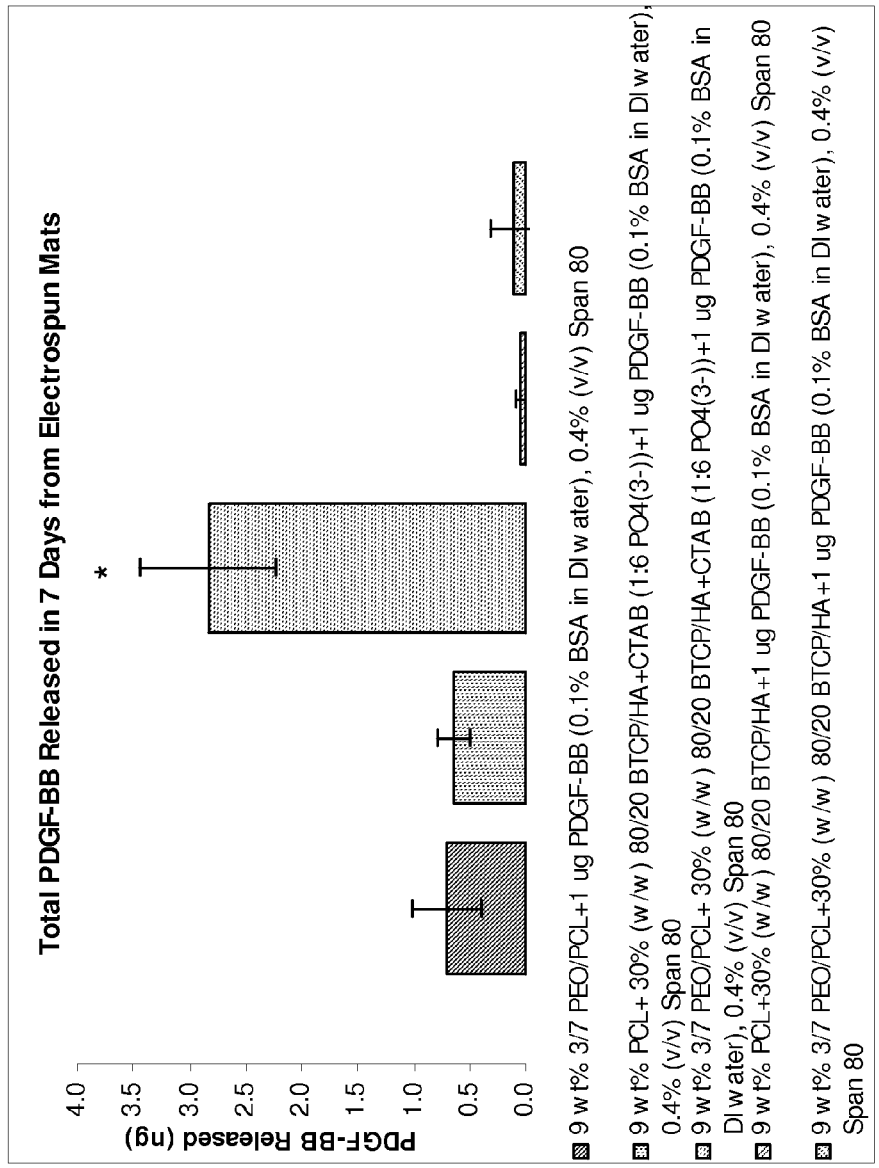
FIG. 4 shows total PDGF-BB released in 7 days from electrospun mats.

In embodiments of the present invention where PDGF-BB was incorporated into the polymer/ceramic electrospun scaffolds, it was discovered that significantly less PDGF-BB was released compared to embodiments prepared without ceramic (FIG. 2). It was hypothesized that this was due electrostatic attraction between the PDGF-BB molecules which have a net positive surface charge and the negative charges of the phosphate ions ($PO_4^{3-}$) in the ceramic, thus impeding the release of PDGF-BB from the polymer/ceramic scaffold. β-TCP/HA was complexed with the cationic surfactant, Cetyl trimethylammonium bromide (CTAB) at molecular ratios 1 CTAB: 1 $PO_4^{3-}$ and 1 CTAB: 6 $PO_4^{3-}$, to partially charge neutralize the phosphate ions and thereby decrease the electrostatic attraction between the phosphate ions and protein in certain embodiments of the present invention. The complexation of CTAB to β-TCP/HA was shown to enhance the quantity of PDGF-BB released from the scaffold compared to polymer/ceramic scaffolds without CTAB (FIGS. 3 and 4).

Figure 5:
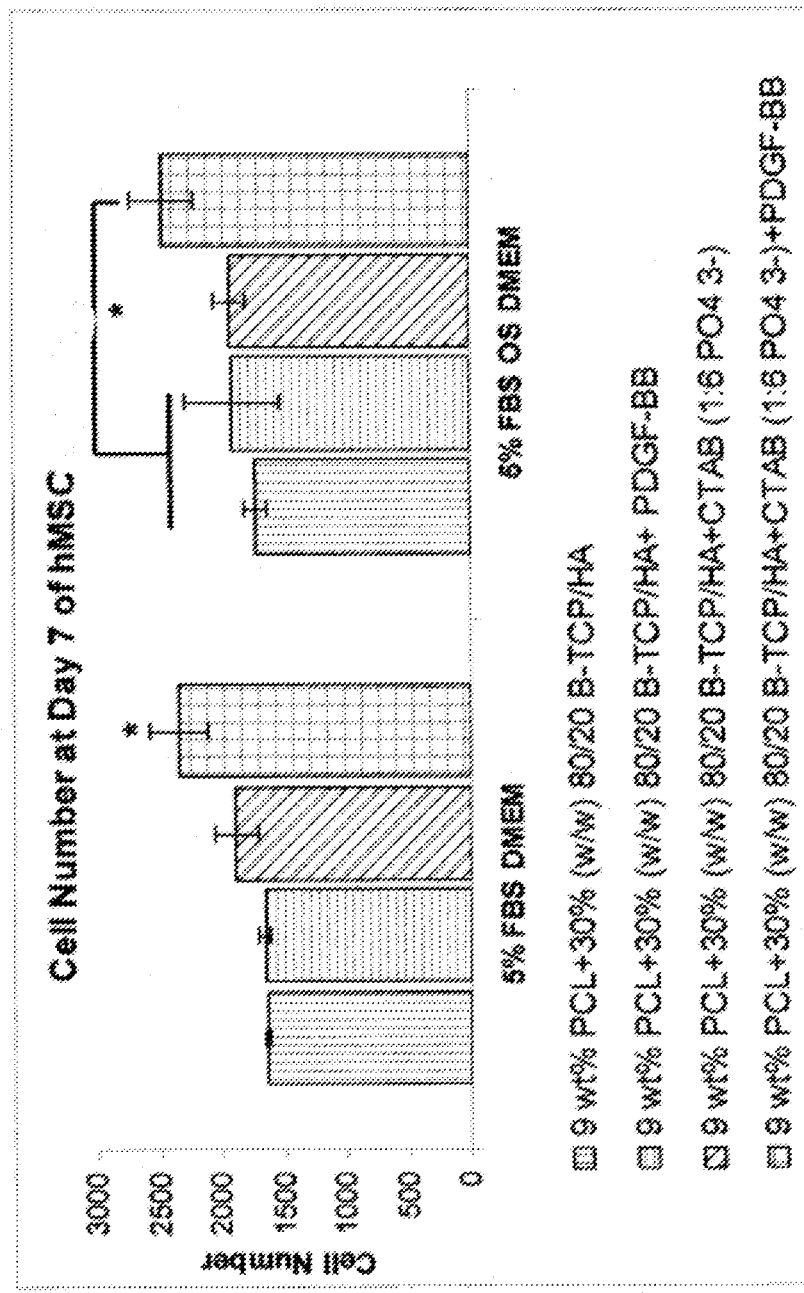
FIG. 5 shows cell number at day 7 of hMSC where asterisks indicate statistical difference between 9 wt % PCL+30% (w/w) 80/20 β-TCP/HA+PDGF-BB compared to other scaffolds in 5% FBS OS DMEM, and 9 wt % PCL+ 30% (w/w) 80/20 β-TCP/HA and 9 wt % PCL+30% (w/w) 80/20 β-TCP/HA+PDGF-BB in 5% FBS OS DMEM.
Figure 6:
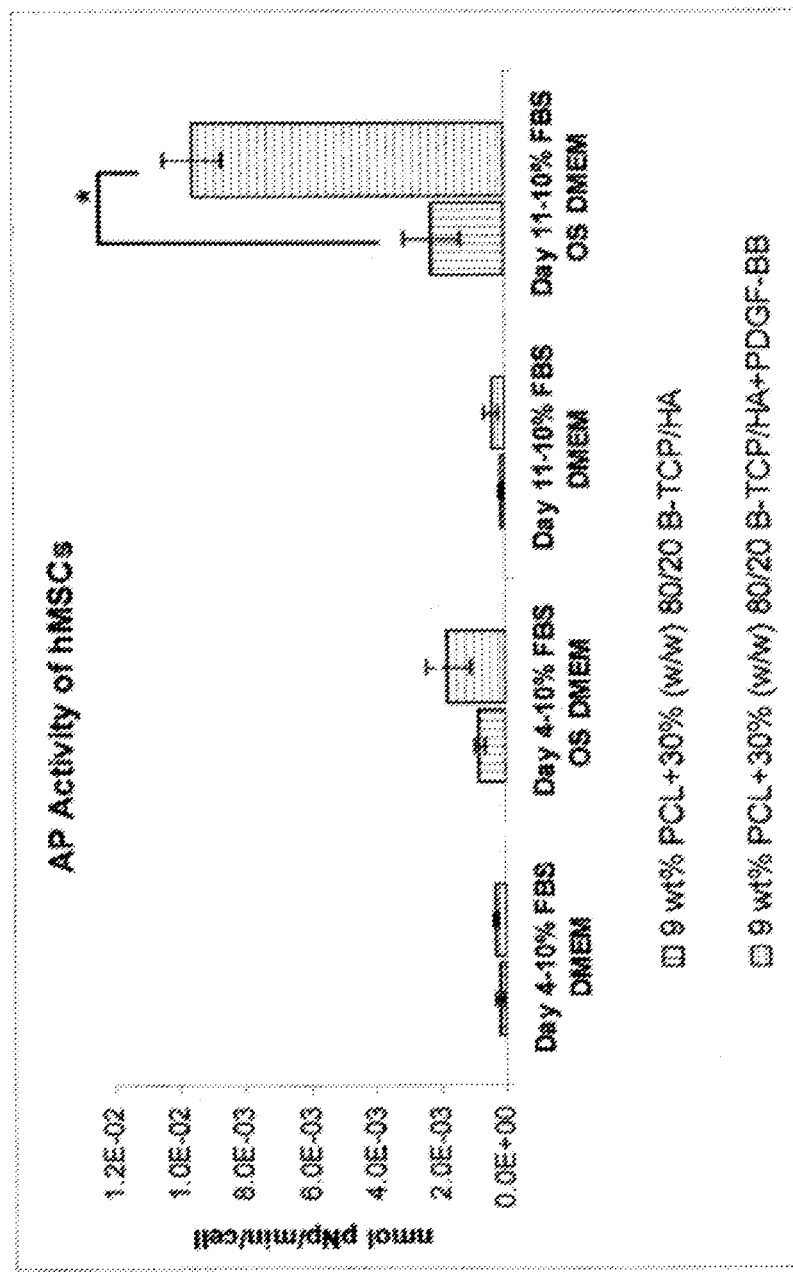
FIG. 6 shows AP activity of hMSCs where asterisks indicate statistical difference between groups 9 wt % PCL+ 30% (w/w) 80/20 β-TCP/HA+PDGF-BB and 9 wt % PCL+ 30% (w/w) 80/20 β-TCP/HA at Day 11 in 10% FBS OS DMEM (p<0.05)
Figure 7:
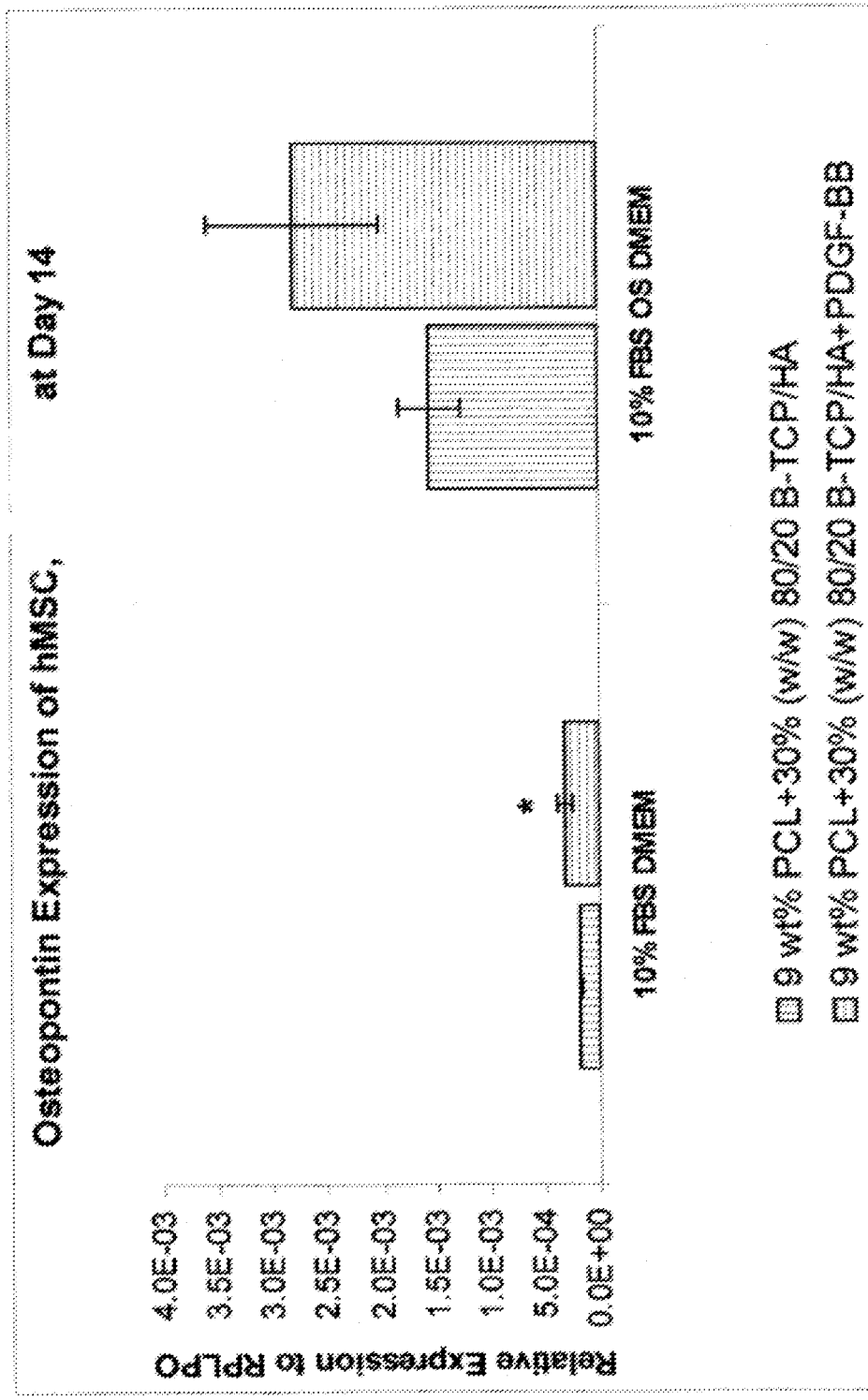
FIG. 7 shows osteopontin expression of hMSC at Day 14, where asterisks indicate statistical difference between 9 wt % PCL+30% (w/w) 80/20 β-TCP/HA and 9 wt % PCL+30% (w/w) 80/20 β-TCP/HA+PDGF-BB in 10% FBS DMEM.
Figure 8:
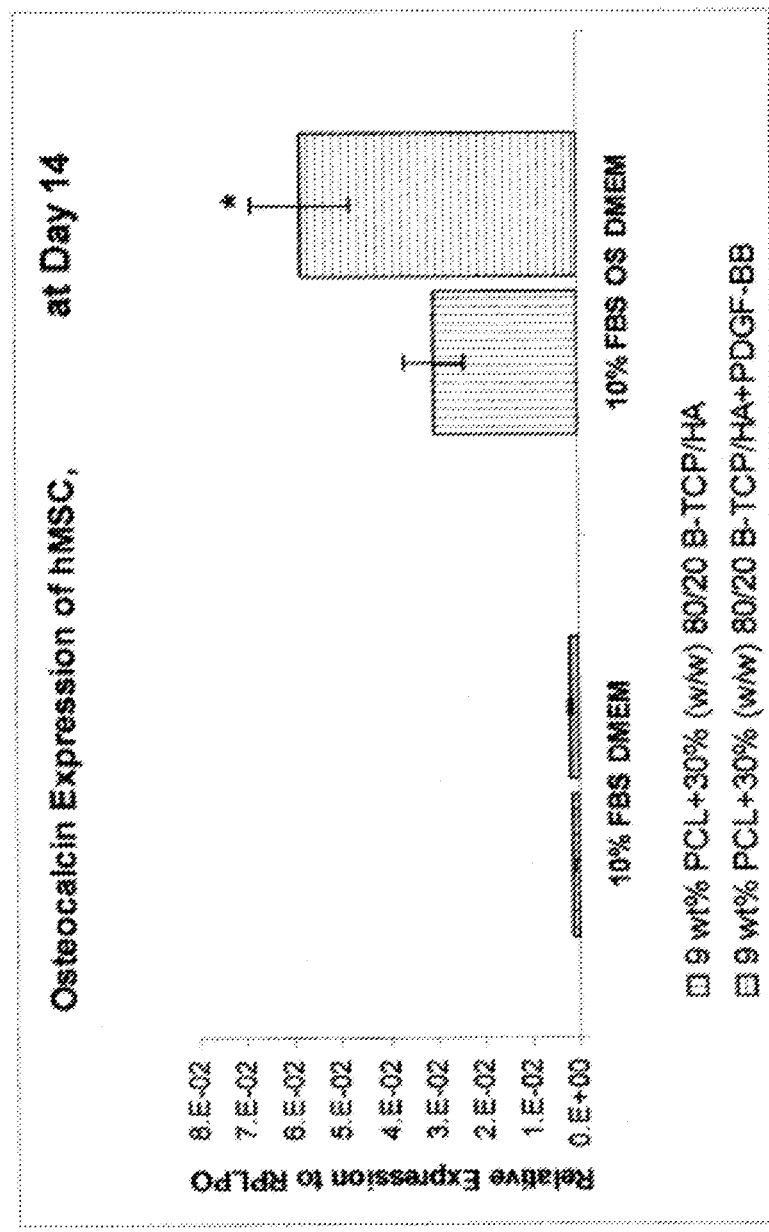
FIG. 8 shows osteocalcin expression of hMSC at Day 14, where asterisks indicate statistical difference between 9 wt % PCL+30% (w/w) 80/20 β-TCP/HA and 9 wt % PCL+30% (w/w) 80/20 β-TCP/HA+PDGF-BB in 10% FBS OS DMEM.

Embodiments of the present invention were further characterized for the ability to support cell proliferation and osteogenic activity using human mesenchymal stem cells (hMSCs). It was shown tha proliferation was higher on embodiments containing PDGF-BB incorporated scaffolds prepared with CTAB (FIG. 5). Scaffold embodiments prepared with PDGF-BB incorporated 9 wt % 3/7 PEO/PCL had higher alkaline phosphatase activity as compared to scaffolds without PDGF-BB. In one preferred embodiment showing favorable osteogenic differentiation of the hMSCs utilized PDGF-BB incorporated 9 wt % PCL+30% (w/w) ceramic (which were prepared without CTAB). Alkaline phosphatase activity was higher in hMSC embodiments seeded on PDGF-BB incorporated 9 wt % PCL+30% (w/w) 80/20 β-TCP/HA as compared to 9 wt % PCL+30% (w/w) 80/20 β-TCP/HA without PDGF-BB embodiments (FIG. 6). Furthermore, the expression of certain osteogenic genes, osteopontin and osteocalcin, were enhanced for hMSC embodiments seeded onto 9 wt % PCL+30% (w/w) 80/20 β-TCP/HA with PDGF-BB as compared to 9 wt % PCL+ 30% (w/w) 80/20 β-TCP/HA embodiments without PDGF-BB (FIGS. 7 and 8).

Although it was determined that PDGF-BB was released at negligible quantities from the polymer/ceramic composites, the data suggests that the PDGF-BB was immobilized onto the scaffold of certain embodiments of the present invention by electrostatic interactions. Said immobilized PDGF-BB was bioactive as determined by the enhanced osteogenic activity of the hMSCs.

In conclusion, a series of embodiments of the present invention comprising novel biodegradable electrospun scaffolds incorporated with PDGF-BB have been developed and implemented for use as possible scaffolds for bone regeneration. Said scaffolds prepared with PEO enhanced the release of PDGF-BB in certain exemplary embodiments of the present invention. Scaffolds containing CTAB significantly increased the quantity of PDGF-BB released from electrospun scaffolds prepared with polymers and ceramic and thus may have enhanced cell proliferation at early time-in certain exemplary embodiments and the most favorable for demonstrating osteogenic activity is the composite scaffold containing the growth factor without the use of PEO and CTAB in vitro conditions.

Materials and Methods

PDGF-BB purchased from Prospec Bio and Invitrogen. Serum starvation studies were then conducted to determine the bioactivity of PDGF-BB purchased from Prospec Bio and Invitrogen. Cell proliferation studies indicated that PDGF-BB from Invitrogen was more bioactive than PDGF-BB from Prospec Bio. Therefore, the PDGF-BB from Invitrogen was used for the subsequent studies.

Direct Addition of PDGF-BB.

The direct addition of PDGF-BB refers to the incorporation of PDGF-BB to polymer solutions that were not emulsified. PDGF-BB was incorporated into non-emulsified polymer solutions to determine the effect of PEO on the release of PDGF-BB from the electrospun mats. The polymer solutions were prepared in chloroform according to the formulations in Table 1. Lyophilized recombinant human PDGF-BB was reconstituted in 100 mM acetic acid for a 0.5 mg/mL solution. 2 μL of the 0.5 mg/mL PDGF-BB solution was pipetted to each polymer solution for a total loading of 1 μg of PDGF-BB. The polymers solutions were mixed on the magnetic stir plate for approximately 20 minutes prior to electro spinning.

TABLE 1

Direct Addition of PDGF-BB Solution Preparation Conditions

| Polymer Concentration | PEO/PCL Ratio | PDGF-BB Vendor | PDGF-BB Concentration | PDGF-BB Loading |
|---|---|---|---|---|
| 9 wt % | 0/100<br>30/70 | Prospec Bio | 0.5 mg/mL, diluted in 100 mM acetic acid | 2 μL containing 1 μg of PDGF-BB |
| 9 wt % | 30/70<br>50/50<br>70/30 | Prospec Bio | 0.5 mg/mL, diluted in 100 mM acetic acid | 2 μL containing 1 μg of PDGF-BB |
| 9 wt % | 30/70<br>50/50<br>70/30 | Prospec Bio | 0.5 mg/mL, diluted in 100 mM acetic acid with 0.1% BSA | 2 μL containing 1 μg of PDGF-BB |
| 9 wt % | 30/70 | Invitrogen | 0.5 mg/mL diluted in 100 mM acetic acid with 0.1% BSA | 2 μL containing 1 μg of PDGF-BB |

Emulsification by Ultrasonication.

Various emulsion preparation conditions were investigated to determine the effect of Span® 80 incorporation and sonication on the release of PDGF-BB from electrospun mats. It was determined that the bioactivity of lysozyme released at 24 hours from emulsions prepared from 9 wt % 30/70 PEO/PCL incorporated with 0.4% (v/v) Span® 80 and sonicated, was statistically higher compared to emulsions prepared by the other conditions.

Lyophilized recombinant human PDGF-BB (Invitrogen) was reconstituted in 100 mM acetic acid with 0.1% BSA for a 0.5 mg/mL solution. The 0.5 mg/mL PDGF-BB solution was further diluted in either 0.1% BSA in PBS or 0.1% BSA in DI water to a final concentration of 10 μg/mL. These emulsions were prepared by pipetting Span® 80 (for Span® 80 incorporated conditions) into chloroform, followed by the addition of the PDGF-BB solution in a drop-wise manner into the chloroform, prior to the addition of the polymers according to the conditions in Table 2. After mixing on the magnetic stir plate for approximately one hour, the polymer solutions were either sonicated on ice with a probe ultrasonicator or left un-sonicated.

Scaffolds for serum starvation studies were prepared with polymer solutions loaded with PDGF-BB at quantities that would theoretically induce cell proliferation upon release.

For these scaffolds, PDGF-BB at a concentration of 100 µg/mL in 0.1% BSA in DI water, was added to the polymer solutions at a loading of approximately 1.1 µg of PDGF-BB per 1 gram of polymer solution or 10 µg of PDGF-BB in 9 grams of polymer solution.

TABLE 2

PDGF-BB Incorporated Emulsion Preparation Conditions

| Polymer Concentration | PEO/PCL Ratio | PDGF-BB Concentration (Invitrogen) | PDGF-BB Loading | Span ® 80 Concentration (with respect to polymer solvent volume) | | Sonication Conditions |
|---|---|---|---|---|---|---|
| 9 wt % | 30/70 | 10 µg/mL, diluted in 0.1% BSA in PBS or DI water | 100 µL containing 1 µg of PDGF-BB | 0.4% (v/v) | 0% (v/v) for conditions without Span ® 80 | Branson Ultrasonifier: 2 minutes pulse mode at 20% amplitude | No sonication |
| 9 wt % | 30/70 | 10 µg/mL, diluted in 0.1% BSA in DI water | 100 µL containing 1 µg of PDGF-BB | 0.4% (v/v) | 0% (v/v) for conditions without Span ® 80 | Branson Ultrasonifier: 2 minutes pulse mode at 10% or 20% amplitude | No sonication |
| 9 wt % | 30/70 | 10 µg/mL, diluted in 0.1% BSA in DI water | 100 µL containing 1 µg of PDGF-BB | 1% (v/v) | 2% (v/v) | Branson Ultrasonifier: 2 minutes pulse mode at 10% amplitude | |
| 9 wt % | 30/70 | 100 µg/mL diluted in 0.1% BSA in DI water | 200 µL containing 20 µg of PDGF-BB | 0.4% (v/v) | | Branson Ultrasonifier: 2 minutes pulse mode at 10% amplitude | |
| 9 wt % | 30/70 | 100 µg/mL diluted in 0.1% BSA in DI water | 100 µL containing 10 µg of PDGF-BB | 0.4% (v/v) | | Branson Ultrasonifier: 2 minutes pulse mode at 10% | |

Electrospinning.

The polymer solutions/emulsions were electrospun in an environmental chamber at 21-23° C. and 17-26% relative humidity. Polymer solutions/emulsions were placed in a 10 mL syringe and passed through a blunt 20 gauge stainless needle at 3.0 mL/hour using a syringe pump (Harvard Apparatus). The applied voltage to the needle tip was 20 kV. The distance between the needle tip to the grounded collection plate was between 20-50 cm, depending upon the polymer solution. Electrospun mats were peeled off from the collector plate and placed in a desiccator until the initiation of the study.

Some of the polymer/ceramic suspensions were electrospun in a non-enclosed electrospinning apparatus which did not have any humidity controls, because it was determined that electrospinning in the enclosed chamber produced undesirable fiber morphologies which may have been a result of residual solvent vapor.

Polymer/ceramic suspensions were placed in a 10 mL syringe and passed through a blunt 20 gauge stainless steel needle at 3.0 mL/hour using a syringe pump (Harvard Apparatus). The applied voltage to the needle tip was 20 kV. The distance between the needle tip to the grounded collection plate was between 30-60 cm, depending upon the suspension.

During the summer, when the bulk of the electrospinning was conducted, the high relative humidity (above 60%) resulted in unpredictable fiber and scaffold morphologies. In a modified electrospinning unit, the water vapor in the air was condensed into liquid and froze onto a cooling probe, leaving dehumidified air inside the electrospinning chamber. Furthermore, an exit diffuser compartment provided an outlet channel to reduce the solvent vapor inside the electrospinning chamber. The relative humidity inside the electrospinning chamber was maintained to below 50% which resulted in desirable fiber morphologies. The syringe pump rate, voltage and distance between needle tip and collector plate were similar to the conditions for electrospinning in the non-enclosed chamber. Electrospun mats were peeled off from the collector plate and placed in a desiccator until the initiation of the study.

The lysozyme incorporated polymer/ceramic suspensions were electrospun in a non-enclosed electrospinning unit. Polymer/ceramic suspensions were placed in a 10 mL syringe and passed through a blunt 20 gauge stainless needle at 3.0 mL/hour using a syringe pump (Harvard Apparatus). The applied voltage to the needle tip was 20 kV. The distance between the needle tip to the grounded collection plate was between 30-60 cm, depending upon the suspension.

PDGF-BB incorporated polymer/ceramic emulsions were electrospun in the modified enclosed electrospinning units with similar parameters outlined above. The PDGF-BB incorporated polymer/ceramic emulsions with CTAB were electrospun in a non-enclosed electrospinning unit with similar parameters outlined in the previous section.

Post-Electrospun PDGF-BB Incorporation.

Polymer solutions were prepared in chloroform and electrospun using the conditions described above. The electrospun mats were cut into 19 mm discs and placed into low attachment 24 well plates (Costar). A 40 µg/mL solution of PDGF-BB (Invitrogen) was prepared in PBS. To each scaffold, 1 mL of the 40 µg/mL PDGF-BB solution was added and then incubated overnight at 37° C., 5% CO2. Following the overnight incubation, the discs were rinsed three times with PBS and placed in a laminar air hood for approximately 7 hours to dry the discs until the initiation of the in vitro release study.

In Vitro Release Studies.

PDGF-BB incorporated electrospun scaffolds were cut into 19 mm discs (n=3) and placed in 24 well low-attachment plates. For some studies, the scaffolds were cut into 6 mm discs (n=3) and placed in 96 well polypropylene plates. At the initiation of the release study, the plates were sterilized with UV light prior to the addition of 0.5 mL of PBS in the 24 well plates and 150-300 µL in the 96 well plates, and then placed in a 37° C., 5% CO2 incubator. At predetermined time-points during the study, the release medium was collected from each well which were replenished with fresh PBS. For some studies, the electrospun discs were dried under a laminar air hood, and dissolved in chloroform to which PBS was added to extract the residual PDGF-BB. For other studies, the residual PDGF-BB was extracted using a protocol described by Sakiyama-Elbert et al. Briefly, dried scaffolds were placed in a solution of 1% BSA, 2M of sodium chloride, and 0.01% Triton-X in PBS and placed in 4° C. for 72 hours, after which the supernatant was collected for the PDGF-BB ELISA.

PDGF-BB Quantitation.

The release media and residual PDGF-BB samples were stored at −20° C. until the PDGF-BB quantitation using a PDGF-BB ELISA (PeproTech). Briefly, 100 µL of the release medium was added to an immunoplate coated with anti-PDGF-BB. The presence of PDGF-BB was detected through the color change of an enzymatic substrate which was detected at 410 nm with an absorbance plate reader. A calibration curve of known PDGF-BB concentrations was used to determine the unknown concentration in the release media.

Percent Weight Change.

The electrospun mats (n=3) were weighed prior to the incubation and placed in wells of a 24 well plate. After the in vitro release study, the electrospun mats were dried and then weighed. The percent weight loss was calculated using Equation 2.4, using the weight at the final time-point.

Visualization of PDGF-BB or Lysozyme in Electrospun Fibers.

Immunofluorescence was used to visualize PDGF-BB incorporated in electrospun mats. Briefly, electrospun scaffolds were cut into 6 mm discs and blocked with 1% BSA in PBS for approximately an hour. Following a rinsing step in PBS, 100 µL of a 2 µg/mL anti-PDGF-BB (R&D Systems) solution in 1% BSA in PBS was added to each mat for approximately an hour. Following another rinsing step, 100 µL of 1 µg/mL Fluorescein-conjugated Rabbit Antigoat secondary antibody (Pierce) in 1% BSA in PBS was added to each mat. For a negative control, electrospun mats were stained with only secondary antibody at 1 µg/mL in 1% BSA in PBS to detect the presence of non-specific staining. The mats were viewed with the confocal microscope at 408 nm excitation/455 nm emission to view the autofluoresced electrospun fibers and 488 nm excitation/515 nm emission to view the secondary antibody stain.

For lysozyme incorporated in electrospun mats, the electrospun scaffolds were stained with the 2 µg/mL of anti-lysozyme primary antibody in 1% BSA in PBS and 1 µg/mL of Alexa Fluor 488 Donkey anti-rabbit IgG secondary antibody in 1% BSA in PBS. For a negative control, designated electrospun mats were stained with the secondary antibody at 1 µg/mL to detect the presence of non-specific staining. The mats were viewed with the confocal microscope at 408 nm excitation/455 nm emission to view the autofluoresced electrospun fibers and 488 nm excitation/515 nm emission to view the secondary antibody stain.

Statistical Analysis.

Quantitated data was represented as the mean±standard deviation. A student's t-test was conducted for the comparison of 2 groups at each timepoint, with significance set to $p<0.05$. One-way ANOVA was performed on data sets with more than 2 groups, collected at a single time-point. The Tukey post-hoc test was conducted to determine differences ($p<0.05$) between pairs. For the CTAB cytotoxicity study, TCPS was not included in the statistical analysis. For data represented as a function of time, a two-way repeated measures ANOVA was conducted to determine the effect of the material and PDGF-BB with time.

Ceramic Preparation.

The weight ratio of 80/20 β-TCP to HA was determined as the ideal ratio to induce the osteogenic differentiation of mesenchymal stem cells. An 80/20 β-TCP/HA suspension was prepared in chloroform and then placed in a water bath sonicator (VWR, Aquasonic 75T) for 2 minutes. The polymer solutions prepared in chloroform were added to the ceramic suspensions for final ceramic concentrations of 9% (w/w), 17% (w/w), 23% (w/w) or 30% (w/w) with respect to polymer mass.

Native Lysozyme Incorporation Through Dissolution in DMSO.

Native lysozyme was dissolved in DMSO and added to the polymer/ceramic suspension according to the conditions listed Table 3, then mixed on a magnetic stir plate overnight followed by electrospinning.

TABLE 3

Polymer/Ceramic Solution Preparation Conditions for Pre-Electrospun Incorporated Lysozyme Dissolved in DMSO

| Polymer Concentration | PEO/PCL Ratio | Concentration of 80/20 β-TCP/HA (with respect to polymer mass) | Lysozyme Concentration (in DMSO) | Lysozyme Loading (with respect to polymer mass) |
|---|---|---|---|---|
| 7.5 wt % | 0/100 25/75 | 9% (w/w) 17% (w/w) | 10 mg/mL | 0.1% (w/w) |

Ultrasonic Emulsification.

Solutions of native lysozyme were prepared in DI water. In Studies B and C, Span® 80 and the aqueous lysozyme solutions were added to the polymer/ceramic suspensions according to the conditions listed in Table 4

TABLE 4

Polymer/Ceramic Emulsion Preparation Conditions for Pre-Electrospun Lysozyme Dissolved in DI water

| Polymer Concentration | PEO/PCL Ratio | Concentration of 80/20 β-TCP/HA (with respect to polymer mass) | Lysozyme Concentration (in DI water) | Lysozyme Loading (with respect to polymer mass) | Span® 80 Concentration (with respect to polymer solvent volume) | Sonication Parameters (Instrument-Conditions) |
|---|---|---|---|---|---|---|
| 7.5 wt % | 0/100 25/75 | 9% (w/w) 17% (w/w) | 10 mg/mL | 0.1% (w/w) | 0.002% (v/v) | Omni-Rupter: 1 minute continuous at 20% amplitude |
| 9 wt % | 0/100 30/70 | 9% (w/w) | 20 mg/mL | 0.2% (w/w) | 0.4% (v/v) | Branson: 2 minutes pulse mode at 20% amplitude |
| 9 wt % | 0/100 30/70 | 23% (w/w) | 20 mg/mL | 0.2% (w/w) | 0.4% (v/v) | Branson: 2 minutes pulse mode at 20% amplitude |

Post-Electrospun Lysozyme Incorporated Polymer/Ceramic Scaffold Preparation.

Prior to electrospinning, polymer/ceramic suspensions were sonicated with a probe ultrasonicator (Sonifier® 5450-D, Branson) at 20% amplitude on pulse mode (1 second on, 1 second off) for 2 minutes, to disperse the ceramic nanoparticles. The electrospun mats were cut into 19 mm discs and placed into low attachment 24 well plates (Costar). The electrospun mats were sterilized with UV light for approximately 30 minutes prior to the addition of 500 µL of a 0.5 mg/mL solution of lysozyme in PBS to each well containing the discs and then placed in a 37° C., 5% CO2 incubator overnight.

Following the overnight incubation, the discs were rinsed three times with PBS and placed in a laminar air hood overnight to dry the discs until the initiation of the in vitro lysozyme release studies.

Preparation of CTAB Modified Polymer/Ceramic Composite Scaffolds.

Cetyl trimethylammonium bromide (CTAB, Sigma) was incorporated to correspond to a molecular ratio of 1 CTAB to 1 phosphate ions (PO4 3−) in 80/20 β-TCP/HA, and 1 CTAB to 6 PO4 3− ions in 80/20 β-TCP/HA. The CTAB and 80/20 β-TCP/HA were mixed in chloroform on a magnetic stir plate for approximately an hour prior to the addition of polymer for a final ceramic concentration of either 23% (w/w) β-TCP/HA with 1:1 CTAB:PO4 3−, renamed 23% (w/w) β-TCP/HA+CTAB (high); and 23% (w/w) β-TCP/HA with 1:6 CTAB:PO4 3−, renamed 23% (w/w) β-TCP/HA+CTAB (low).

CTAB was incorporated to correspond to a molecular ratio of 1 CTAB to 6 PO4 3− in 80/20 β-TCP/HA. The CTAB and β-TCP/HA were mixed in chloroform on a magnetic stir plate for approximately an hour prior to the addition of polymer for a final ceramic concentration of 30% (w/w) 80/20 β-TCP/HA with 1:6 CTAB:PO4 3−, renamed 30% (w/w) β-TCP/HA+CTAB.

CTAB Cytotoxicity Study.

The PicoGreen® ds DNA quantitation assay (Invitrogen) was conducted to determine whether cells seeded on CTAB containing scaffolds maintained viability.

Cell Culture Studies.

Electrospun mats of PCL+23% (w/w) β-TCP/HA+CTAB (high) and PCL+23% (w/w) β-TCP/HA+CTAB (low) were cut into 6 mm discs (n=3) and placed in polypropylene 96 well plates. The scaffolds were compared to PCL, 30/70 PEO/PCL, PCL+23% (w/w) β-TCP/HA, and 30/70 PEO/PCL+23% (w/w) β-TCP/HA, and Tissue Culture Polystyrene (TCPS) which served as the control. All scaffolds were sterilized with UV light for 30 minutes. (Refer to section 5.1.1.1 for detailed instructions on hMSC isolation) One vial of hMSCs, Donor 7, passage 3 was thawed, and suspended in Dulbecco's Modified Eagle Medium (DMEM) containing 10% Fetal Bovine Serum (FBS). Cells were seeded at a density of 12,500 cells/cm2, which was 3500 cells per well. The cells were incubated at 37° C., 5% CO2 and harvested at Days 3 and 7 for the PicoGreen assay. Cell lysates were prepared by lysing cells on scaffolds and TCPS in 0.1% Triton X-100. The PicoGreen reagent fluorescently labels double stranded DNA which was correlated to cell number using a standard curve. The PicoGreen reagent was added to the cell lysates and the fluorescence was detected with a plate reader at 485 nm excitation/528 nm emission.

Ceramic Preparation.

A suspension of 80/20 β-TCP/HA was prepared in chloroform and then placed in a water bath sonicator for 2 minutes. The polymer solutions prepared in chloroform were added to the ceramic suspensions for final ceramic concentrations of 30% (w/w) with respect to polymer mass.

CTAB modified Ceramic Preparation. PDGF-BB Incorporation.

The PDGF-BB incorporated polymer/ceramic scaffolds were prepared by ultrasonic emulsification according to the parameters in Table 5. Briefly, lyophilized recombinant human PDGF-BB (Invitrogen) was reconstituted in 100 mM acetic acid with 0.1% BSA for a 0.5 mg/mL solution. The 0.5 mg/mL PDGFBB solution was further diluted in 0.1% BSA in DI water to a final concentration of 10 µg/mL for a loading of 1 µg per mat or a concentration of 100 µg/mL for the therapeutic loading of 10 µg per mat (1.1 µg of PDGF-BB/ gram of polymer/ceramic emulsion).

TABLE 5

Study Design for PDGF-BB Incorporated Polymer/Ceramic Electrospun Scaffolds

| Polymer Concentration | PEO/PCL Ratio | Concentration of 80/20 β-TCP/HA (with respect to polymer mass) | CTAB Incorporation | PDGF-BB Concentration (Invitrogen) | PDGF-BB Loading | Span ® 80 Concentration (with respect to polymer solvent volume) | Sonication Conditions |
|---|---|---|---|---|---|---|---|
| 9 wt % | 0/100 30/70 | 30% (w/w) | None | 10 μg/mL in 0.1% BSA in DI water | 10 μL for a loading of 1 μg | 0.4% (v/v) | Branson Ultrasonifier: 2 minutes pulse mode at 10% amplitude |
| 9 wt % | 0/100 30/70 | 30% (w/w) | 1 CTAB: 6 $PO_4^{3-}$ | 10 μg/mL in 0.1% BSA in DI water | 10 μL for a loading of 1 μg | 0.4% (v/v) | Branson Ultrasonifier: 2 minutes pulse mode at 10% amplitude |
| 9 wt % | 0/100 30/70 | 30% (w/w) | None, 1 CTAB: 6 $PO_4^{3-}$ | 100 μg/mL in 0.1% BSA in DI water | 100 μL for a loading of 10 μg | 0.4% (v/v) | Branson Ultrasonifier: 2 minutes pulse mode at 10% amplitude |

In Vitro PDGF-BB Release Study.

The PDGF-BB incorporated electrospun scaffolds were cut into 19 mm discs (n=3) and placed in 24 well low-attachment plates. For some studies, the electrospun mats were cut into 6 mm discs and placed in 96 well polypropylene plates (Nunc). At the initiation of the release study, the plates were sterilized with UV light prior to the addition of 0.5 mL of PBS for Studies A-B or 150 μL of PBS for Study C and then placed in a 37° C., 5% CO2 incubator. At pre-determined time-points during the study, the release medium was collected from each well which were replenished with fresh PBS.

Isolation and Culture of Human Mesenchymal Stem Cells.

Human mesenchymal stem cells (hMSCs) were isolated from commercially obtained (Cambrex) bone marrow aspirates collected from the superior iliac crest of the pelvis of male donors. The isolation method described in detail by Haynesworth, proceeds with washing the marrow sample with PBS followed by centrifugation in a 70% density gradient solution at 13,000 g for 20 minutes. The hMSC fraction was collected and then plated into tissue culture polystyrene flasks (Nunc) with Dulbecco's Modified Eagle Medium (DMEM, Invitrogen) containing 10% FBS (Hyclone) and 1% Antibiotic-Antimycotic (Invitrogen): "10% FBS DMEM", then placed in a 37° C., 5% CO2 humidified incubator. On average, confluency of hMSCs was achieved within 12-16 days. At the point of near confluency, cells were detached from the substrate with 0.25% Trypsin-EDTA (Invitrogen). Cells were resuspended in 10% FBS DMEM and centrifuged at 900 g for 5 minutes. The cells were then collected and placed into a new tissue culture flask. This procedure called serial passaging or subculturing was done up to a maximum of 4 passages. After each passage, cells were cryopreserved in freezing medium containing 90% FBS and 10% Dimethyl Sulfoxide (DMSO). The cryopreserved cells were stored in a liquid nitrogen tank until the initiation of the study.

PDGF-BB and Cell Culture Media Preparation.

At the initiation of this study, arbitrarily called "Day −2", a vial of hMSCs was thawed, resuspended in 10% FBS DMEM, and seeded into 96 well TCPS plates at a seeding density of 12,500 cells/cm2 or 4000 cells/well. On "Day −1", 24 hours following the initial cell seeding, the media in the wells was changed with DMEM prepared with various concentrations of FBS (Table 6). On Day 0, the media was supplemented with various concentrations of PDGF-BB (Prospec Bio or Invitrogen). PDGF-BB supplementation was done either once at Day 0, or continually for every 48-72 hours until Day 7.

TABLE 6

Serum Starvation Study Conditions
Table 5.1 Serum Starvation Study Conditions

| | | | |
|---|---|---|---|
| Concentration of FBS in DMEM at "Day −2" | 10% FBS | 10% FBS | 10% FBS |
| Concentration of FBS in DMEM at "Day −1" | 2% FBS | 5% FBS | 10% FBS |
| Concentration of PDGF-BB supplemented to x% FBS in DMEM at "Day 0" | 2% FBS DMEM + No PDGF-BB 25 ng/mL PDGF-BB 50 ng/mL PDGF-BB 100 ng/mL PDGF-BB | 5% FBS DMEM + No PDGF-BB 25 ng/mL PDGF-BB 50 ng/mL PDGF-BB 100 ng/mL PDGF-BB | 10% FBS DMEM + No PDGF-BB 25 ng/mL PDGF-BB 50 ng/mL PDGF-BB 100 ng/mL PDGF-BB |
| Frequency of PDGF-BB addition | "Day 0" only Continuous: Every 48-72 hours | "Day 0" only Continuous: Every 48-72 hours | "Day 0" only Continuous: Every 48-72 hours |

Cell Proliferation.

At Days 4 and 7 following growth factor induction, cells were harvested for cell proliferation assay. Briefly, cell lysates (n=3 per media and PDGF-BB condition) were prepared by lysing cells in 0.1% Triton X-100. The PicoGreen reagent fluorescently labels double stranded DNA which was correlated to cell number using a standard curve. The PicoGreen reagent was added to the cell lysates and the fluorescence was detected with a plate reader at 485 nm excitation/528 nm emission.

Alkaline Phosphatase Activity.

The activity of Alkaline Phosphatase (AP) was determined by quantifying the conversion rate of para-nitrophenyl phosphate (p-Npp) to para-nitrophenol (p-Np). Standards of known p-Np concentrations were prepared in phosphatase buffer. Cell lysates prepared in 0.1% Triton X-100, and standards were incubated at 37° C. for 30 minutes in a water bath. The absorbance of the samples and standards was read at 405 nm with an absorbance plate reader. The AP activity was normalized to cell number determined from the PicoGreen assay (nmol of p-Np/min/cell).

Cell Seeding on Transwell Membranes.

The design of the transwell bioactivity studies was modeled after the serum starvation studies. At "Day -2", a vial of hMSCs, Donor 7, passage 2, was thawed and resuspended in 10% FBS DMEM. The cells were seeded at a density of 12,500 cell/cm2 or 4000 cells/well in 100 μL of media on 0.4 μm transwell membrane inserts (Corning) which were placed in a low attachment 24 well plate. At "Day -1", the media in designated wells was replaced with 5% FBS DMEM, other designated wells remained in 10% FBS DMEM for control. At Day 0, the electrospun scaffold: PEO/PCL incorporated with 1.1 μg PDGF-BB/gram of polymer solution, was cut into 19 mm discs (n=3), and placed at the bottom of designated wells of which 500 μL of 5% FBS DMEM was added to. The transwell membrane inserts were placed on top of the wells containing the scaffold. For positive control, 10 ng/mL of PDGF-BB was added to cells cultured in 5% FBS DMEM.

At 4, 7 and 11 days following growth factor induction, the cells were harvested from the inserts with 0.1% Triton X-100 for the PicoGreen assay, following the methods described in the previous section.

Cell Seeding.

A list of electrospun scaffolds used in the cell/scaffold studies is listed in Table 7.

hMSC, Donor 7, passage 2, was thawed and seeded onto the scaffolds at a density of 4000 cells/well in 10% FBS DMEM. After 24 hours of initial hMSC seeding, the media in the wells containing the scaffolds was replaced with either 5% FBS DMEM or "5% FBS OS DMEM" which was 5% FBS DMEM supplemented with 10 mM beta glycerophosphate (Sigma), 50 μM L-ascorbic acid phosphate (Wako) and 100 nM of dexamethasone (Sigma) to induce osteogenic differentiation.

For other studies, cryopreserved hMSC was thawed and seeded onto scaffolds at a density of 4000 cells/well in 10% FBS DMEM. Instead of 5% FBS DMEM, the media in the wells containing the scaffolds were maintained in either 10% FBS DMEM or "10% FBS OS DMEM" which was 10% FBS DMEM supplemented with osteogenic components. The cells were replenished with fresh media every 48-72 hours.

For the control groups, hMSCs were seeded in 96 well TCPS plates and cultured in 10% FBS DMEM. After 24 hours of initial cell seeding, the media in the wells was replaced with either basal DMEM (5% FBS or 10% FBS) or the appropriate OS DMEM (5% FBS or 10% FBS). For a positive control group, hMSCs were seeded in 96 well TCPS plates and cultured in basal DMEM. After 24 hours of initial cell seeding, the media was replaced with either basal or OS DMEM supplemented with 10 ng/mL PDGFBB.

In all studies, at Day 12, the media in the wells designated for OS DMEM was replaced with basal DMEM supplemented 10 nM Vitamin D3, 10 mM β-GP and 5 μM ascorbic acid for the duration of the 21 day study to induce osteocalcin production.

Cell Proliferation.

Cells were harvested from the scaffolds for the Picogreen DNA assay with 0.1% Triton X-100 at various time-points of the 21 day study at days 4, 7, 11, 14, and 21.

Osteocalcin Assay.

Cell lysates collected at Days 14 and 21 from Study B were assayed for the osteocalcin production with the human Osteocalcin ELISA kit (Invitrogen). Briefly, an aliquot of the cell lysates was added to the immunoplate. The osteocalcin was detected by the color change of the enzymatic substrate which was read by an absorbance plate reader at 450 nm. A calibration curve of known osteocalcin concentrations was used to determine the concentration of osteocalcin in the cell lysates.

TABLE 7

Electrospun Scaffolds used in the Cell/Scaffold Studies

Scaffold Composition
Ratio of PEO/PCL in blends was 30/70
Concentration of β-TCP/HA was 30% (w/w) 80/20 β-TCP/HA
CTAB concentration was (1:6 $PO_4^{3-}$)

| | Without PDGF-BB | With PDGF-BB (1.1 μg PDGF-BB/g polymer solution), and 0.4% (v/v) Span ® 80 |
|---|---|---|
| Polymer | PCL | PEO/PCL |
| | PEO/PCL | |
| Polymer/ceramic | PCL + β-TCP/HA | PCL + β-TCP/HA |
| | PEO/PCL + β-TCP/HA | PEO/PCL + β-TCP/HA |
| Polymer/ceramic + CTAB | PCL + β-TCP/HA + CTAB | PCL + β-TCP/HA + CTAB |
| | PEO/PCL + β-TCP/HA + CTAB | PEO/PCL + β-TCP/HA + CTAB |

Electrospun scaffolds were cut into 6 mm discs and placed in 96 well polypropylene plates. At the initiation of the study, on Day 0, the scaffolds were sterilized with UV light for approximately 30 minutes. For Study A, cryopreserved Gene Expression.

For Studies B and C, the cells seeded on the scaffolds and TCPS were harvested for the gene expression studies. At days 0, 7 and 14, cells were harvested for RNA isolation using the RNeasy® Micro kit (Qiagen, Valencia, Calif.). Briefly, RNA was eluted from the homogenized cells harvested from the substrates. For each target or housekeeping gene, a master-mix consisting of primers and reagents from the Sybr Green RT-PCR kit (Qiagen) was prepared according the manufacturer's instructions, and added to the isolated RNA. The reverse transcription of the RNA and polymerization of cDNA was performed on a thermal cycler (MX3000P, Stratagene) using the following conditions of: 30 minutes at 50° C., 15 minutes at 95° C., 40 cycles of 15 seconds at 94° C., 30 seconds at 55° C. and 72° C., followed by 1 minute at 95° C. and 41 cycles at 55° C. The target genes that investigated in this study were: Osteocalcin (OCN), Osteopontin (OPN), Collagen Type I (Col I), Sox2, Runx2. Relative quantification of a replicate of three samples per group, was obtained by normalizing the expression of each target gene to the expression of the housekeeping gene (large ribosomal protein, RPLPO) using the Q-gene software. Melting curves were used to evaluate the integrity of the amplified cDNA, and samples with compromised melting curve due to the presence of "primer dimers" were not used for analysis.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

The invention claimed is:

1. An electrospun composite scaffold comprising a polyester, a hydrophilic polymer, a bioceramic that includes phosphate ions, a cationic surfactant that complexes with the phosphate ions of the bioceramic, and a growth factor or a protein, wherein complexing of the cationic surfactant with the phosphate ions of the bioceramic decreases electrostatic attraction of the growth factor or the protein to the bioceramic, thereby enhancing release of the growth factor or the protein from the scaffold relative to release from the same scaffold without a cationic surfactant.

2. The electrospun composite scaffold of claim 1, wherein the polyester is selected from the group consisting of polylactic acid, polyglycolic acid, polylactic co-glycolic acid copolymers and polycaprolactone.

3. The electrospun composite scaffold of claim 1, wherein the hydrophilic polymer is selected from the group consisting of polyethylene oxide, polyethylene glycol, polyvinyl alcohol, glycosaminoglycans, chitosan, sulfated dextran, sulfated cellulose, and heparin sulfate.

4. The electrospun composite scaffold of claim 1, wherein the growth factor is selected from the group consisting of Recombinant human Platelet Derived Growth Factor-BB (PDGF-BB), vascular endothelial factor (VEGF), transforming growth factor-beta (tgf-BETA) and Bone Morphogenetic Protein (BMP).

5. The electrospun composite scaffold of claim 1, wherein the protein is lysozyme.

6. The electrospun composite scaffold of claim 1, wherein the bioceramic is selected from the group consisting of hydroxyapatite, tricalcium phosphate, and biphasic calcium phosphate.

7. The electrospun composite scaffold of claim 1, wherein the cationic surfactant is cetyl trimethylammonium bromide (CTAB).

* * * * *